United States Patent
Zhao et al.

(10) Patent No.: US 11,712,457 B2
(45) Date of Patent: Aug. 1, 2023

(54) *SYRINGA PUBESCENS MICROPHYLLA* SEED EXTRACT COMPOSITION AND ITS APPLICATION IN ANTIBIOTIC-RESISTANT INFECTIONS

(71) Applicants: Qianqian Zhao, Xi'an (CN); Jialin Li, Xi'an (CN); Dan Yang, Xi'an (CN); Jingyi Li, Xi'an (CN); Liang Xin, Xi'an (CN); Chunyang Shi, Xi'an (CN); Xiaolin Xie, Xi'an (CN); Dezhu Zhang, Xi'an (CN); Ruina Bian, Xi'an (CN); Xingke Ju, Xi'an (CN); Chengyuan Liang, Xi'an (CN); Yanjun Li, Xi'an (CN); Qiao Zeng, Xi'an (CN)

(72) Inventors: Qianqian Zhao, Xi'an (CN); Jialin Li, Xi'an (CN); Dan Yang, Xi'an (CN); Jingyi Li, Xi'an (CN); Liang Xin, Xi'an (CN); Chunyang Shi, Xi'an (CN); Xiaolin Xie, Xi'an (CN); Dezhu Zhang, Xi'an (CN); Ruina Bian, Xi'an (CN); Xingke Ju, Xi'an (CN); Chengyuan Liang, Xi'an (CN); Yanjun Li, Xi'an (CN); Qiao Zeng, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 70 days.

(21) Appl. No.: 17/173,622

(22) Filed: Feb. 11, 2021

(65) Prior Publication Data
US 2022/0160805 A1 May 26, 2022

(30) Foreign Application Priority Data
Nov. 25, 2020 (CN) .......................... 202011344016.6

(51) Int. Cl.
| | | |
|---|---|---|
| *A61K 36/63* | (2006.01) | |
| *A61P 31/04* | (2006.01) | |
| *A61K 47/44* | (2017.01) | |
| *A61K 31/7034* | (2006.01) | |
| *A61K 31/7048* | (2006.01) | |

(52) U.S. Cl.
CPC .......... *A61K 36/63* (2013.01); *A61K 31/7034* (2013.01); *A61K 31/7048* (2013.01); *A61K 47/44* (2013.01); *A61P 31/04* (2018.01); *A61K 2236/15* (2013.01); *A61K 2236/333* (2013.01); *A61K 2236/35* (2013.01); *A61K 2236/37* (2013.01); *A61K 2236/51* (2013.01); *A61K 2236/53* (2013.01)

(58) Field of Classification Search
CPC ................ A61K 36/63; A61K 31/7034; A61K 31/7048; A61K 47/44; A61K 2236/15; A61K 2236/333; A61K 2236/35; A61K 2236/37; A61K 2236/51; A61K 2236/53; A61K 2236/33; A61K 2236/39; A61P 31/04
See application file for complete search history.

(56) References Cited

FOREIGN PATENT DOCUMENTS

| | | | |
|---|---|---|---|
| CN | 107802676 | * | 3/2018 |
| CN | 109021041 A | * | 12/2018 |
| KR | 10-2011-0074004 | * | 10/2011 |

OTHER PUBLICATIONS

Wozniak, M. et al. Effects of Phytochemically Characterized Extracts from *Syringa vulgaris* . . . Frontiers in Pharmacology 9(349)1-15, 2018. (Year: 2018).*
Toth, G. et al. Characterization of Antioxidant Phenolics in *Syringa vulgaris* L. . . . Biomedical Chromatography 30(6)923-932, Jun. 2016. (Year: 2016).*
Yang, D. et al. Syringa microphylla Diels . . . Phytomedicine 93:1-28 2021. (Year: 2021).*
Deng, R. et al. Chemical Constituents from Syringa pubescens Turcz. Biochemical Systematics and Ecology 38(4)813-815, 2010. (Year: 2010).*

* cited by examiner

*Primary Examiner* — Aaron J Kosar

(57) ABSTRACT

A *Syringa microphylla* seed extract includes the following components by weight based on a total weight of the *Syringa microphylla* seed extract: 0.4944-0.7142 mg/g of echinacoside, 6.624-7.617 mg/g of oleuropein, 0.4276-0.6309 mg/g of verbascoside, 3.927-4.684 mg/g of syringin, and 4.505-5.250 mg/g of forsythiaside B. A method of preparing the *Syringa microphylla* seed extract is disclosed. A composition for treating antibiotic-resistant infections that includes the *Syringa microphylla* seed extract is also disclosed.

1 Claim, 4 Drawing Sheets

SYRINGA PUBESCENS MICROPHYLLA SEED EXTRACT COMPOSITION AND ITS APPLICATION IN ANTIBIOTIC-RESISTANT INFECTIONS

The present invention claims priority to Chinese Patent Application No. CN 202011344016.6, filed on Nov. 25, 2020, which are incorporated by reference for all purposes as if fully set forth herein.

FIELD OF THE INVENTION

The present invention relates to a *Syringa pubescens microphylla* seed extract, its preparation and application in antibiotic-resistant infections.

BACKGROUND OF THE INVENTION

With the widespread use of antibiotics around the world, the overuse of antibiotics has become increasingly common, and microorganisms that have developed tolerance to the corresponding antibiotics have emerged, posing a new threat to human health. The emergence of antibiotic-resistant bacteria has increased the difficulty of curing infectious diseases. At present, both gram-positive bacteria and gram-negative bacteria have a drug resistance trend, and the problem of drug resistance of gram-positive bacteria is more serious. Methicillin-resistant *Staphylococcus aureus* (MRSA) is a common clinically toxic bacterium. Since its discovery, the infection has spread almost all over the world, and it is a very difficult problem in clinical anti-infective treatment. The development of new antibacterial drugs is urgent. Many pharmaceutical companies in the world are actively looking for new drugs that can treat antibiotic-resistant infections.

*Syringa pubescens microphylla* is a shrub of the Oleaceae family, also known as Qiaolinghua, *Buxus*, and *Lilac*. It is distributed in the provinces of Henan, Hebei, Shaanxi, Shanxi, and Gansu in China, growing in the mountains at an altitude of 800-2400 m. Its flowers and fruits are used to make tea. In recent years, most studies on the chemical composition and pharmacological effects of *Syringa pubescens microphylla* have been on the bark. There are few reports on the chemical components and pharmacological activities of *Syringa pubescens microphylla* seeds.

SUMMARY OF THE INVENTION

In one embodiment, the present application provides a *Syringa pubescens microphylla* seed extract that includes the following components by weight based on a total weight of the *Syringa pubescens microphylla* seed extract: 0.4944-0.7142 mg/g of echinacoside, 6.624-7.617 mg/g of oleuropein, 0.4276-0.6309 mg/g of verbascoside, 3.927-4.684 mg/g of syringin, and 4.505-5.250 mg/g of forsythiaside B.

In another embodiment, a method for preparing the *Syringa pubescens microphylla* seed extract includes the following steps: S1, obtaining *Syringa pubescens microphylla* seeds, pulverizing, and passing through a sieve to obtain a seed powder; S2, extracting the seed powder with petroleum ether, heating under reflux, filtering to obtain a residue, and extracting the residue with methanol to obtain a methanol extract; and S3, concentrating the methanol extract to obtain the *Syringa pubescens microphylla* seed extract.

In another embodiment, in step S2, the seed powder is extracted with petroleum ether two times, 8 hours each time; and the residue is extracted with methanol two times, 4 hours each time.

In another embodiment, a composition for treating antibiotic-resistant infections includes: the *Syringa pubescens microphylla* seed extract and a pharmaceutically acceptable carrier or diluent.

In another embodiment, the pharmaceutically acceptable carrier or diluent is one or more selected from the group consisting of olive oil, corn oil, castor oil, cotton seed oil, oil from wheat with germ, cacao oil, white soft paraffin, solid paraffin, liquid paraffin, hohoba oil, carnauba wax, lauric acid, myristic acid, palmitic acid, stearic acid, oleic acid, linoleic acid, linolenic acid, polyethylene glycol and polyoxyethylene alcohol.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Reference will now be made in detail to embodiments of the present invention, example of which is illustrated in the accompanying drawings. The following examples illustrate the present invention, but the present invention is not limited to the following examples.

Figure 1:
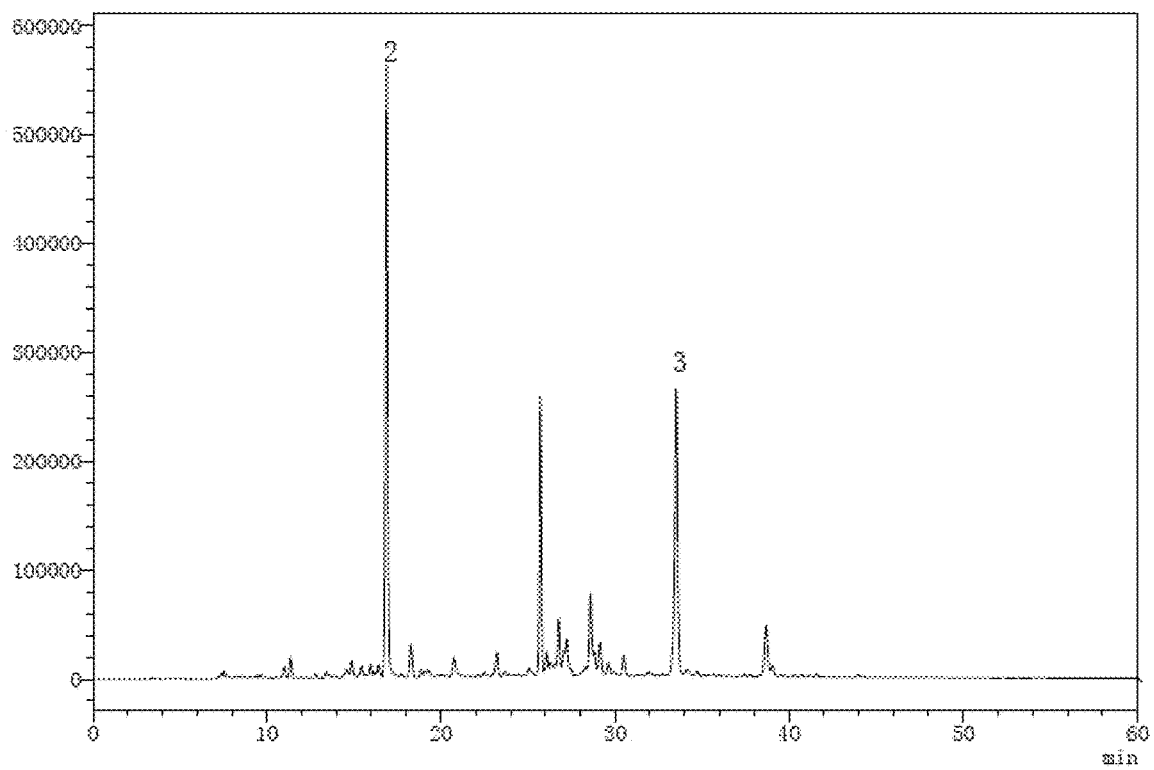
FIG. 1 is an HPLC spectrum of *Syringa pubescens microphylla* extract at a wavelength of 254 nm.

As shown in FIG. 1, the embodiment of the present invention provides an EtOH-Water extract with standardized chemical composition of the large-leaf ash tree seed, which contains the following components by mass percentage:

The *Syringa pubescens microphylla* seed extract of the present application, based on the total weight of the *Syringa pubescens microphylla* seed extract, includes the following components by weight: 0.4944-0.7142 mg/g of echinacoside (Compound 4), 6.624-7.617 mg/g of oleuropein (Compound 3), 0.4276-0.6309 mg/g of verbascoside (Compound 5), 3.927-4.684 mg/g of syringin (also known as eleutheroside B, Compound 2), and 4.505-5.250 mg/g of forsythiaside B (Compound 1).

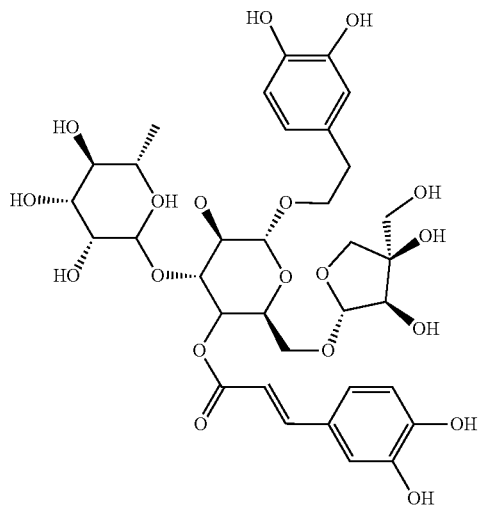

1

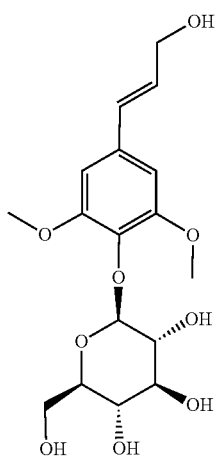

2

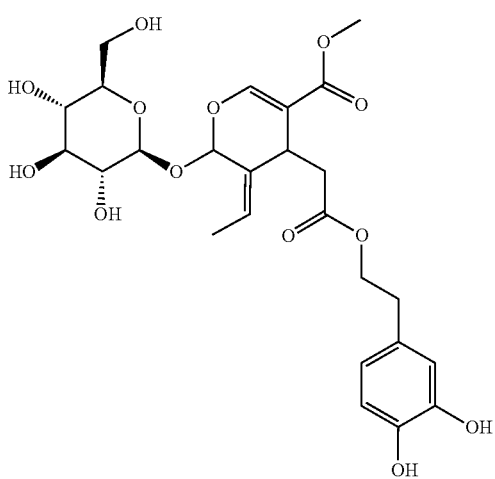

3

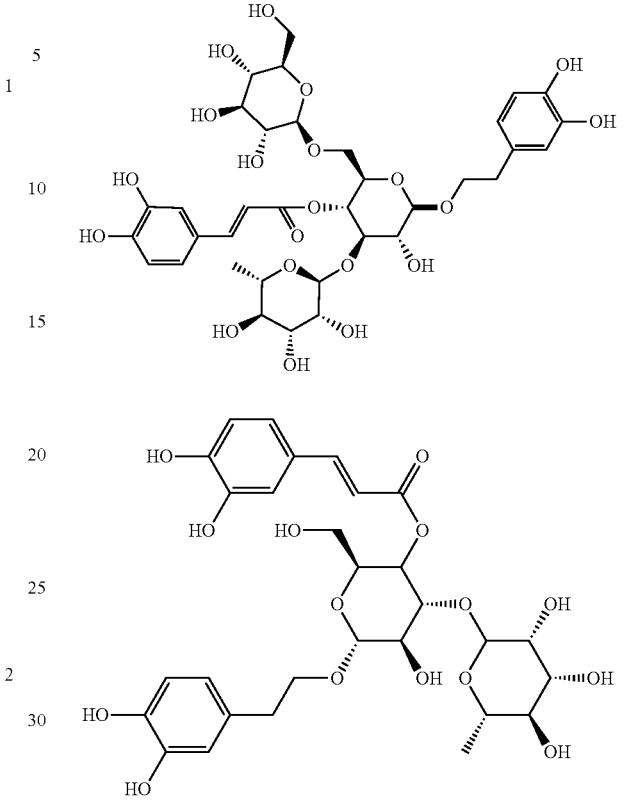

4

5

The present application also provides a method for preparing the *Syringa pubescens microphylla* seed extract. The method includes the following steps:

S1, obtaining 1 kg of *Syringa pubescens microphylla* seeds, pulverizing, and passing through a sieve to obtain a seed powder;

S2, extracting the seed powder with petroleum ether and heating under reflux twice, 8 hours each time, filtering to obtain a residue, extracting the residue with methanol twice, and 4 hours each time, combining the methanol solution to obtain a methanol extract; and S3, concentrating the methanol extract to obtain the *Syringa pubescens microphylla* seed extract.

The present application uses a drug sensitive paper method to evaluate the antibacterial activity of the *Syringa pubescens microphylla* seed extract. The results show that the *Syringa pubescens microphylla* seed extract significantly inhibit multi-drug resistant bacteria. Therefore, the *Syringa pubescens microphylla* seed extract of the present invention can be used for the development and application of drugs for the treatment of antibiotic-resistant infections.

EXAMPLES

*Syringa pubescens microphylla* seed were collected from Song County, Luoyang City, Henan Province, China; reference materials were purchased from China Food and Drug Control Institute; methanol and petroleum ether were of chromatography grade; water was of ultra-pure grade; and all solvents were filtered with 0.45 μm microporous membrane before using. Other reagents were of analytical grade.

Preparing Sample Solutions 1 kg of *Syringa pubescens microphylla* seeds were pulverized and passed through a sieve to obtain a seed powder. The seed powder was extracted with petroleum ether and heated under reflux twice, 8 hours each time, filtered to obtain a residue. The residue was dried and extracted with methanol twice, and 4 hours each time. The methanol solution was combined to obtain a methanol extract. The methanol extract was concentrated to obtain the *Syringa pubescens microphylla* seed extract. 1 mL of the seed extract was filtered with 0.45 μm microporous membrane to obtain a *Syringa pubescens microphylla* seed extract solution, ready for use.

Certain amounts of forsythiaside B (Compound 1), syringin (Compound 2), oleuropein (Compound 3), echinacoside (Compound 4), and verbascoside (Compound 5) were dissolved in methanol to prepare five reference sample solutions, respectively. See Table 1. 10 μL of sample solution was injected to into a liquid chromatograph: column temperature: 30° C.; flow rate: 1 mL/min; wavelength: 254 nm and 330 nm dual wavelength; sample volume: 10 μL; chromatographic column: Kromasil 100-5-C18; column length: 250×4.6 mm; mobile phase A: 1% phosphoric acid aqueous solution; mobile phase B: acetonitrile; elution gradient: 0 min: A 95%, B 5%, 15 min: A 85%, B 15%, 20 min: A 80%, B 20%, 30 min: A 75%, B 25%, 60 min: A 60%, B 40%.

The peak area was measured, concentration (μg/ml) as X-axis, and peak area integral value as Y-axis (compound 2 and compound 3 measured at a wavelength of 254 nm; compound 1, compound 4 and compound 5 measured at a wavelength of 330 nm). Standard curves and correlation coefficients were calculated and shown in Table 2, and the five compounds have a good linear relationship ($R^2>0.999$).

TABLE 1

Concentrations of 5 Reference Compound Solutions (μg/ml)

| Compounds | 1 | 2 | 3 | 4 | 5 |
|---|---|---|---|---|---|
| 1. forsythiaside B | 50 | 100 | 250 | 500 | 1000 |
| 2. syringin | 50 | 100 | 250 | 500 | 1000 |
| 3. oleuropein | 50 | 100 | 200 | 400 | 800 |
| 4. echinacoside | 5 | 10 | 20 | 40 | 80 |
| 5. verbascoside | 5 | 10 | 20 | 40 | 80 |

TABLE 2

Linear Relationship of Reference Compound Solutions

| Compounds | Standard Curve | $R^2$ | Concentration (μg/ml) |
|---|---|---|---|
| 1. forsythiaside B | Y = 12172.0X + 133648 | 0.9996 | 50-1000 |
| 2. syringin | Y = 17909.5X − 18125.0 | 0.9998 | 50-1000 |
| 3. syringin | Y = 6179.83X − 73300.0 | 0.9995 | 50-800 |
| 4. echinacoside | Y = 7297.89X − 10509.8 | 0.9997 | 5-80 |
| 5. verbascoside | Y = 14772.4X − 3111.27 | 0.9992 | 5-80 |

Compound 2 was used as an example of standard solution
A sample recovery method (1:1 addition) was used. 0.3325 mg of compound 2 was added six methanol solutions of compound 2 with known concentration. 10 μL from each of the six sample solutions was injected into a liquid chromatograph: column temperature: 30° C.; flow rate: 1 mL/min; wavelength: 254 nm and 330 nm dual wavelength; sample volume: 10 μL; chromatographic column: Kromasil 100-5-C18; column length: 250×4.6 mm; mobile phase A: 1% phosphoric acid aqueous solution; mobile phase B: acetonitrile; elution gradient: 0 min: A 95%, B 5%, 15 min: A 85%, B 15%, 20 min: A 80%, B 20%, 30 min: A 75%, B 25%, 60 min: A 60%, B 40%. The recovery rates were calculated. The results show that the average recovery rate was 98.91% and the RSD was 2.333%.

TABLE 3

Recovery Results

| Amount in Solution (mg) | Added Amount (mg) | Measurement (mg) | Recovery (%) | RSD (%) |
|---|---|---|---|---|
| 0.333 | 0.3325 | 0.6556 | 97.19% | |
| 0.333 | 0.3325 | 0.6528 | 96.33% | 2.333 |
| 0.332 | 0.3325 | 0.6528 | 96.34% | |
| 0.332 | 0.3325 | 0.6698 | 101.44% | |
| 0.333 | 0.3325 | 0.6687 | 101.12% | |
| 0.333 | 0.3325 | 0.6683 | 101.02% | |

The same six standard sample solutions were measured 6 times in succession. The RSD (n=6) of the chromatographic peak area of compound 2 was 1.12%, indicating that the instrument has good accuracy and reproducibility.

TABLE 4

Relative Standard Deviation Results

| | NO. | | | | | | RSD |
|---|---|---|---|---|---|---|---|
| | 1 | 2 | 3 | 4 | 5 | 6 | (%) |
| Peak Area | 5986644 | 6002471 | 5834805 | 6016435 | 5971783 | 5882402 | 1.12 |

Six portions of 1.5 g of *Syringa pubescens microphylla* seeds were used to prepare six 20 mL *Syringa pubescens microphylla* extracts. The content of compound 2 was measured, and the average and the RSD were then calculated. See Table 5. The average concentration of compound 2 in the sample was 4.601 mg/g, and RSD (n=6) was 1.42%, indicating that this method has good reproducibility.

TABLE 5

Reproducibility Results

| Seeds Amount (g) | Peak Area | Concentration (mg/g) | Average (mg/g) | RSD (%) |
|---|---|---|---|---|
| 1.5012 | 6249888 | 4.666434388 | | |
| 1.5033 | 6273961 | 4.684356347 | | |
| 1.5041 | 6134885 | 4.580816513 | 4.60147656 | 1.42 |
| 1.5020 | 6055102 | 4.521419358 | | |
| 1.5002 | 6085334 | 4.543926594 | | |
| 1.5013 | 6176645 | 4.611906158 | | |

Figure 2:
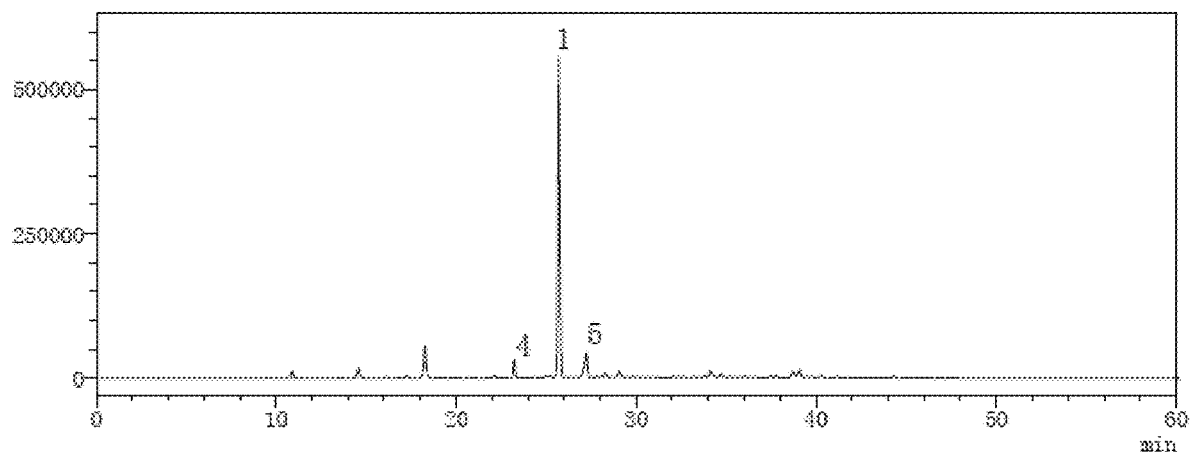
FIG. 2 is an HPLC spectrum of *Syringa pubescens microphylla* extract at a wavelength of 330 nm.

Under the same liquid chromatograph conditions, 12 batches of compounds 1-5 were measured. The results of first batch are shown in FIG. 1 and FIG. 2. The results and calculated average concentrations (standard solutions) are shown in Table 6.

TABLE 6

Concentrations of Compounds 1-5

| Compounds/ | Concentration (mg/g, n = 12) | | | | |
|---|---|---|---|---|---|
| Batches | 1 | 2 | 3 | 4 | 5 |
| (1) | 4.973 | 4.666 | 7.198 | 0.7142 | 0.4276 |
| (2) | 5.250 | 4.684 | 7.617 | 0.6896 | 0.6285 |
| (3) | 5.241 | 4.422 | 7.535 | 0.6032 | 0.6304 |
| (4) | 5.244 | 4.522 | 7.522 | 0.6014 | 0.6309 |
| (5) | 4.531 | 4.020 | 6.624 | 0.4944 | 0.5251 |
| (6) | 5.134 | 4.581 | 7.460 | 0.5734 | 0.6101 |
| (7) | 5.208 | 4.521 | 7.485 | 0.5764 | 0.6165 |
| (8) | 4.991 | 4.332 | 7.189 | 0.5631 | 0.5994 |
| (9) | 4.942 | 4.368 | 7.193 | 0.5381 | 0.5752 |
| (10) | 5.089 | 4.543 | 7.409 | 0.5756 | 0.6140 |
| (11) | 4.505 | 3.927 | 6.519 | 0.5136 | 0.5387 |
| (12) | 5.163 | 4.612 | 7.496 | 0.5835 | 0.6156 |
| Average | 5.023 | 4.433 | 7.271 | 0.5855 | 0.5843 |

Figure 3:
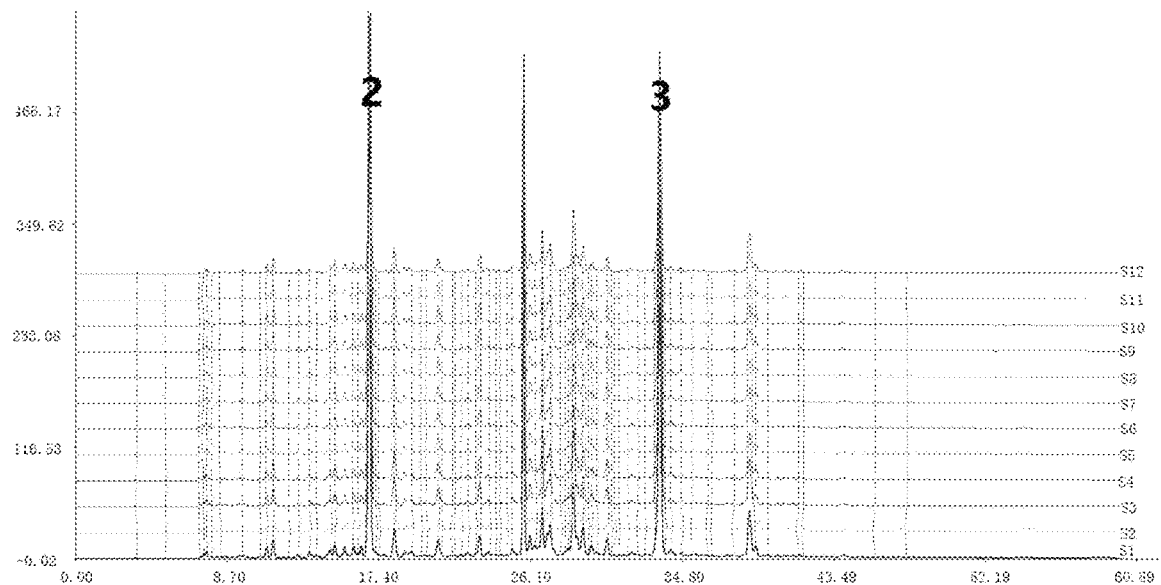
FIG. 3 is a fingerprint spectrum of *Syringa pubescens microphylla* extract at a wavelength of 254 nm.
Figure 4:
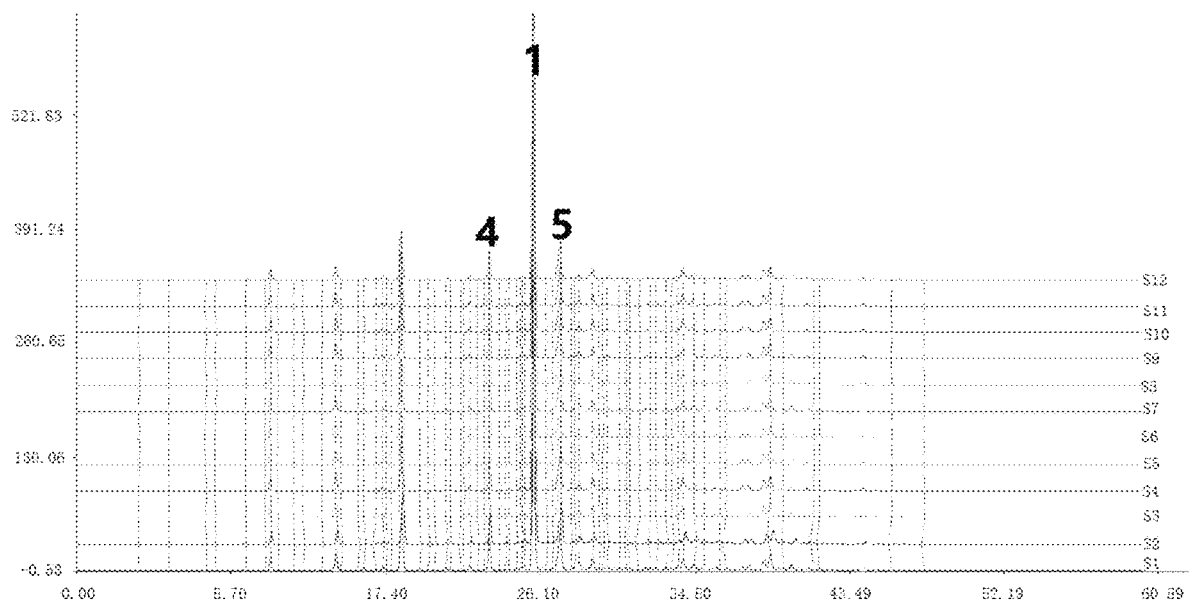
FIG. 4 is a fingerprint spectrum of *Syringa pubescens microphylla* extract at a wavelength of 330 nm.

Preparing Fingerprint Spectra:

The fingerprint spectra were generated based on the results of 12 batches of compounds 1-5 (standard solutions), and are shown in FIG. 3 and FIG. 4.

Analysis of Fingerprint Spectra of Multiple Batches of *Syringa pubescens microphylla* Extracts Twelve batches of *Syringa pubescens microphylla* extracts were measured under the same liquid chromatograph conditions. The *Syringa pubescens microphylla* extract spectra were compared with the fingerprint spectra of the standard solutions. The similarity between the *Syringa pubescens microphylla* extracts and the standard solutions is greater than or equal to 0.85 (See, Table 7 and Table 8). The results show that the similarity of different batches of the *Syringa pubescens microphylla* extracts is relatively high. The fingerprint analysis method established by the invention is stable, reliable and adaptable.

TABLE 7

Fingerprint Spectrum Similarity Analysis (254 nm)

| | S1 | S2 | S3 | S4 | S5 | S6 | S7 | S8 | S9 | S10 | S11 | S12 | Standard |
|---|---|---|---|---|---|---|---|---|---|---|---|---|---|
| S1 | 1 | 1 | 0.995 | 1 | 1 | 1 | 1 | 1 | 1 | 1 | 1 | 1 | 1 |
| S2 | 1 | 1 | 0.995 | 1 | 1 | 1 | 1 | 1 | 1 | 1 | 1 | 1 | 1 |
| S3 | 0.995 | 0.995 | 1 | 0.995 | 0.994 | 0.995 | 0.995 | 0.995 | 0.995 | 0.995 | 0.995 | 0.995 | 0.995 |
| S4 | 1 | 1 | 0.995 | 1 | 1 | 1 | 1 | 1 | 1 | 1 | 1 | 1 | 1 |
| S5 | 1 | 1 | 0.994 | 1 | 1 | 1 | 0.999 | 1 | 0.999 | 1 | 0.999 | 1 | 1 |
| S6 | 1 | 1 | 0.995 | 1 | 1 | 1 | 1 | 1 | 1 | 1 | 1 | 1 | 1 |
| S7 | 1 | 1 | 0.995 | 1 | 0.999 | 1 | 1 | 1 | 1 | 1 | 1 | 1 | 1 |
| S8 | 1 | 1 | 0.995 | 1 | 1 | 1 | 1 | 1 | 1 | 1 | 1 | 1 | 1 |
| S9 | 1 | 1 | 0.995 | 1 | 0.999 | 1 | 1 | 1 | 1 | 1 | 1 | 1 | 1 |
| S10 | 1 | 1 | 0.995 | 1 | 1 | 1 | 1 | 1 | 1 | 1 | 1 | 1 | 1 |
| S11 | 1 | 1 | 0.995 | 1 | 0.999 | 1 | 1 | 1 | 1 | 1 | 1 | 1 | 1 |
| S12 | 1 | 1 | 0.995 | 1 | 1 | 1 | 1 | 1 | 1 | 1 | 1 | 1 | 1 |
| Standard | 1 | 1 | 0.995 | 1 | 1 | 1 | 1 | 1 | 1 | 1 | 1 | 1 | 1 |

TABLE 8

Fingerprint Spectrum Similarity Analysis (330 nm)

| | S1 | S2 | S3 | S4 | S5 | S6 | S7 | S8 | S9 | S10 | S11 | S12 | Standard |
|---|---|---|---|---|---|---|---|---|---|---|---|---|---|
| S1 | 1 | 1 | 0.996 | 1 | 1 | 1 | 1 | 1 | 1 | 1 | 1 | 1 | 1 |
| S2 | 1 | 1 | 0.996 | 1 | 1 | 1 | 1 | 1 | 1 | 1 | 1 | 1 | 1 |
| S3 | 0.996 | 0.996 | 1 | 0.996 | 0.996 | 0.996 | 0.996 | 0.996 | 0.996 | 0.996 | 0.996 | 0.996 | 0.996 |
| S4 | 1 | 1 | 0.996 | 1 | 1 | 1 | 1 | 1 | 1 | 1 | 1 | 1 | 1 |
| S5 | 1 | 1 | 0.996 | 1 | 1 | 1 | 0.999 | 1 | 0.999 | 1 | 0.999 | 1 | 1 |
| S6 | 1 | 1 | 0.996 | 1 | 1 | 1 | 1 | 1 | 1 | 1 | 1 | 1 | 1 |
| S7 | 1 | 1 | 0.996 | 1 | 0.999 | 1 | 1 | 1 | 1 | 1 | 1 | 1 | 1 |
| S8 | 1 | 1 | 0.996 | 1 | 1 | 1 | 1 | 1 | 1 | 1 | 1 | 1 | 1 |
| S9 | 1 | 1 | 0.996 | 1 | 0.999 | 1 | 1 | 1 | 1 | 1 | 1 | 1 | 1 |
| S10 | 1 | 1 | 0.996 | 1 | 1 | 1 | 1 | 1 | 1 | 1 | 1 | 1 | 1 |
| S11 | 1 | 1 | 0.996 | 1 | 0.999 | 1 | 1 | 1 | 1 | 1 | 1 | 1 | 1 |
| S12 | 1 | 1 | 0.996 | 1 | 1 | 1 | 1 | 1 | 1 | 1 | 1 | 1 | 1 |
| Standard | 1 | 1 | 0.996 | 1 | 1 | 1 | 1 | 1 | 1 | 1 | 1 | 1 | 1 |

Antibacterial Activity Test of the Compound of the Present Invention

The bacteriostatic activity test experiment was carried out on the *Syringa pubescens microphylla* extract of the present invention, and the bacteriostatic effect was determined by a paper diffusion drug sensitivity method.

Experimental strains: *Staphylococcus aureus* (SAU), multi-drug resistant *Staphylococcus aureus* 18-206, multi-drug resistant *Pseudomonas aeruginosa* 18-261. The experimental strains were provided by Huashan Hospital, Fudan University (Institute of Antibiotics, Fudan University).

Drug sensitive paper: The drug sensitive paper is a special drug sensitive paper with a diameter of 6.35 mm and a water absorption of 0.02 mL. The control drugs were cefazolin sodium (30 μg/tablet), vancomycin (30 μg/tablet) and gentamicin (30 μg/tablet); the test drug was the *Syringa pubescens microphylla* extract (128 μg/tablet).

Reagents: LB agar medium, LA broth medium, 0.5% DMSO solution.

Equipment: ultra-clean workbench, autoclave, gas bath constant temperature shaking incubator.

Preparation of Bacterial Suspension:

The experimental strains were inoculated in a non-selective medium and incubated in air at 37 C for 24 hours. A single colony was selected and inoculated into a broth medium, and incubated at 35±2° C. for 6 hours. LA broth medium was used to correct the concentration of the bacterial solution to $1.5 \times 10^8$ CFU/mL to obtain a bacterial suspension.

Drug Susceptibility Test by the Paper Diffusion Method:

Weighing LB dry powder, autoclaving at 103.4 Kpa, 121.3° C. for 15 min, then placing in a 40° C.-50° C. water bath. Sterile empty plates (with an inner diameter of 9 cm) were placed on a water platform of the ultra-clean table. LB solution was poured to the plates, with agar thickness of 3 mm-4 mm. After the plates were cooled at room temperature, they were stored in a refrigerator at 2° C. to 8° C. Bacteria liquid was spread evenly with a sterile cotton swab on the surface of the LB plate 3 times. The LB plate was dried at room temperature for 3 min to 5 min. An antibacterial drug paper sheet was placed in the plate using sterile tweezers. The plates were placed in a 37° C. incubator for 24 h. The diameter of inhibition zone was measured. 0.5% DMSO solution was used as the negative control. The diameter of inhibition zone was to measure the antibacterial activity. Inhibition zone≥17 mm, sensitive; inhibition zone=15 mm-16 mm, intermediate; inhibition zone≤14 mm, resistant.

The experimental results are shown in Table 9.

TABLE 9

Zone of Inhibition Results

| Compounds | Diameter of Inhibition Zone / mm Bacteria | | |
|---|---|---|---|
| | SAU | 18-171 | 18-261 |
| 0.5% DMSO | 0 | 0 | 0 |
| cefazolin sodium | 10 | 0 | 0 |
| vancomycin | 23 | 17 | / |
| gentamicin | 18 | 16 | 17 |
| *Syringa pubescens* extract | 10 | 20 | 18 |

Figure 5:
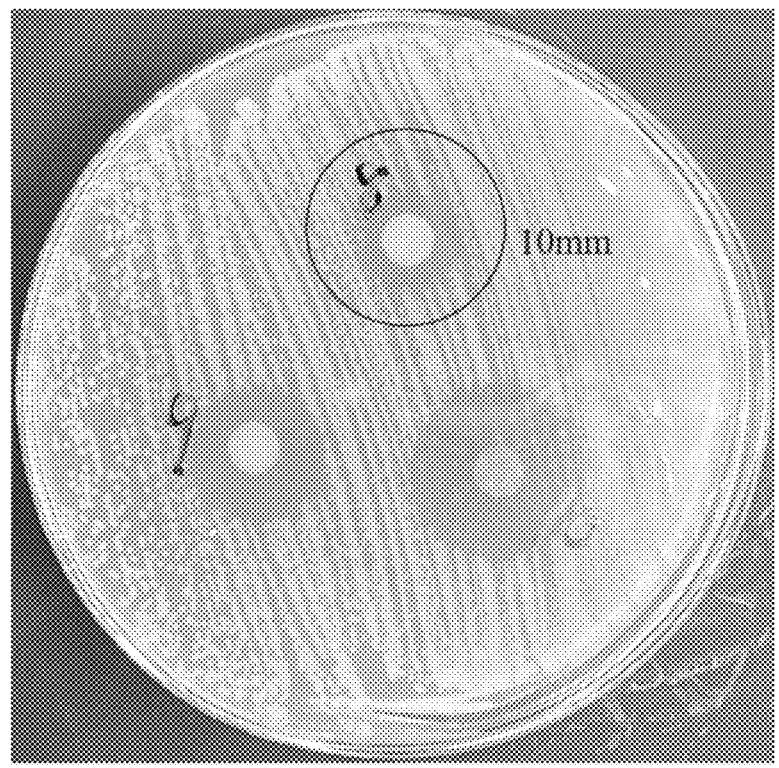
FIG. 5 is an experimental diagram showing the antibacterial activity of *Syringa pubescens microphylla* extract against *Staphylococcus aureus;*
Figure 6:
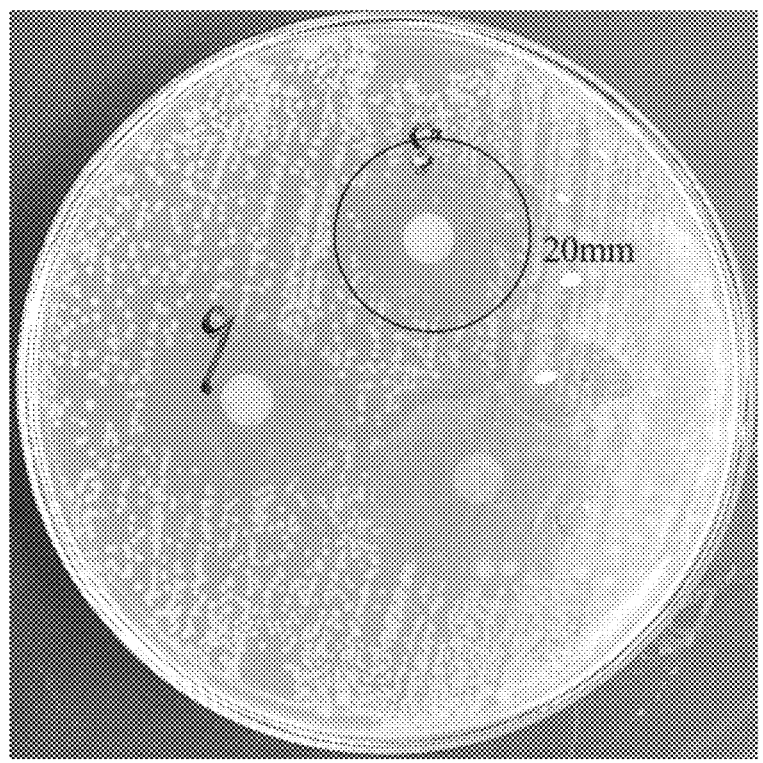
FIG. 6 is an experimental diagram showing the antibacterial activity of *Syringa pubescens microphylla* extract against antibiotic-resistant *Staphylococcus aureus* 18-171.
Figure 7:
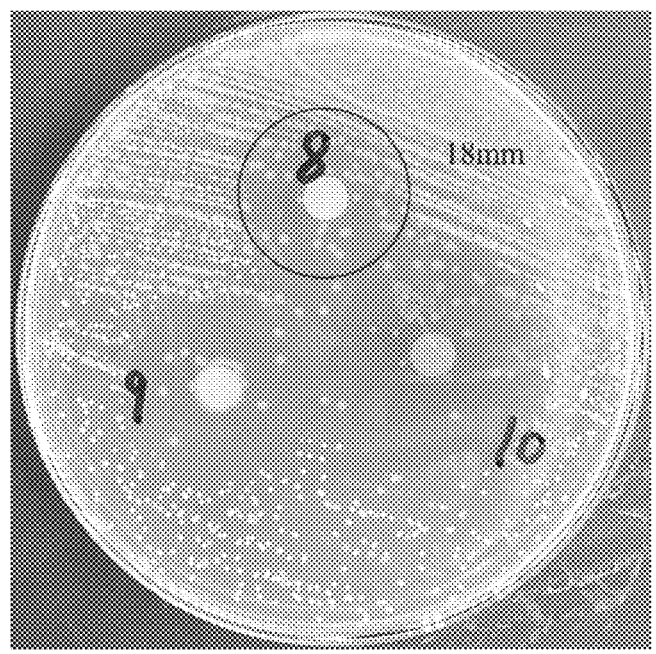
FIG. 7 is an experimental diagram showing the antibacterial activity of antibiotic-resistant against drug-resistant *Pseudomonas aeruginosa* 18-261.

As shown in FIGS. 5-7 and Table 9, the *Syringa pubescens microphylla* extract show has a strong inhibitory effect on multi-drug resistant *Staphylococcus aureus* 18-206 and multi-drug resistant *Pseudomonas aeruginosa* 18-261. In summary, the *Syringa pubescens microphylla* extract of the present invention can be used as an antibacterial drug candidate for multi-drug-resistant *Staphylococcus aureus* and multi-drug-resistant *Pseudomonas aeruginosa*, and further preclinical research can be conducted.

The above are only the preferred embodiments of the present invention. It should be pointed out that for those of ordinary skill in the art, without departing from the principle of the present invention, several improvements and modifications can be made, and these improvements and modifications should also be made. It is regarded as the protection scope of the present invention.

What is claimed is:

1. A composition for treating antibiotic-resistant infections, comprising in a dosage form and therapeutically effective amounts therefor:
   (i) a *Syringa pubescens microphylla* seed extract,
      wherein the seed extract has the identifying features of a *Syringa pubescens microphylla* seed methanolic extract prepared by treating said seed with sequential steps of pulverizing, sieving, extracting with petroleum ether, heating under reflux, filtering, and extracting with said methanol, and
      wherein the seed extract comprises based on a total weight thereof: 0.4944-0.7142 mg/g of echinacoside; 6.624-7.617 mg/g of oleuropein; 0.4276-0.6309 mg/g of verbascoside; 3.927-4.684 mg/g of syringin; and 4.505-5.250 mg/g of forsythiaside B; and
   (ii) a pharmaceutically acceptable carrier or diluent, wherein the pharmaceutically acceptable carrier or diluent is one or more selected from the group consisting of olive oil, corn oil, castor oil, cotton seed oil, wheat germ oil, cacao oil, white soft paraffin, solid paraffin, liquid paraffin, carnauba wax, lauric acid, myristic acid, palmitic acid, stearic acid, oleic acid, linoleic acid, linolenic acid, polyethylene glycol, and polyoxyethylene alcohol; and
   wherein the dosage form is a powder or tablet.

* * * * *